United States Patent
Zardini

(10) Patent No.: US 9,393,600 B2
(45) Date of Patent: Jul. 19, 2016

(54) MACHINE FOR WASHING OBJECTS AND METHOD FOR THE HYDRAULIC AND MECHANICAL CONNECTION OF A TROLLEY CARRYING OBJECTS TO BE WASHED TO A FEED CIRCUIT OF A WASHING LIQUID FOR A MACHINE FOR WASHING OBJECTS

(71) Applicant: STEELCO SPA, Riese Pio X (IT)

(72) Inventor: Fabio Zardini, Castelfranco Veneto (IT)

(73) Assignee: STEELCO SPA, Riese Pio X (TV) (IT)

( * ) Notice: Subject to any disclaimer, the term of this patent is extended or adjusted under 35 U.S.C. 154(b) by 162 days.

(21) Appl. No.: 14/357,339

(22) PCT Filed: Nov. 9, 2012

(86) PCT No.: PCT/IB2012/002283
§ 371 (c)(1),
(2) Date: May 9, 2014

(87) PCT Pub. No.: WO2013/068822
PCT Pub. Date: May 16, 2013

(65) Prior Publication Data
US 2014/0311535 A1    Oct. 23, 2014

(30) Foreign Application Priority Data

Nov. 11, 2011   (IT) .............................. UD2011A0182

(51) Int. Cl.
*B08B 3/04*   (2006.01)
*A61L 2/26*   (2006.01)
*A61B 1/12*   (2006.01)

(52) U.S. Cl.
CPC . *B08B 3/04* (2013.01); *A61B 1/123* (2013.01); *A61L 2/26* (2013.01); *A61L 2202/17* (2013.01); *A61L 2202/24* (2013.01); *Y10T 29/494* (2015.01)

(58) Field of Classification Search
None
See application file for complete search history.

(56) References Cited

U.S. PATENT DOCUMENTS

| | | | | |
|---|---|---|---|---|
| 5,964,955 | A | * | 10/1999 | Rochette ................... B08B 3/02 134/198 |
| 2010/0170544 | A1 | * | 7/2010 | Casonato .............. A47L 15/508 134/137 |

FOREIGN PATENT DOCUMENTS

| | | | |
|---|---|---|---|
| DE | 19627762 | 1/1998 | |
| IT | WO 2008029222 A2 * | 3/2008 | ............ A47L 15/508 |

(Continued)

OTHER PUBLICATIONS

Steelco, "Washer Disinfector", Oct. 14, 2011, XP002668155, pp. 30-31.

*Primary Examiner* — Michael Barr
*Assistant Examiner* — Cristi Tate-Sims
(74) *Attorney, Agent, or Firm* — Hamre, Schumann, Mueller & Larson, P.C.

(57) ABSTRACT

A device according to the present invention can be used for the hydraulic and mechanical connection of a distributor circuit of washing liquid of a trolley carrying objects to be washed to a feed circuit of a washing liquid for a washer machine for objects. The washer machine provides a washing chamber in which to position the trolley which has at least a lateral wall with respect to the direction of insertion of the trolley into the washing chamber. The device comprises a connection member of the distributor circuit, a corresponding delivery or coupling mouth of the feed circuit provided on said lateral wall and at least a connection bushing associable on one side to the connection member of the distributor circuit and on the other side to a corresponding delivery or coupling mouth of the feed circuit that faces inside a washing chamber of the washer machine, so as to determine the mechanical and hydraulic connection between feed circuit and distributor circuit. The device comprises at least an actuator unit that selectively cooperates with said at least one connection bushing, and is configured to act in a first drive direction. The cooperation between actuator unit and said at least one connection bushing is determined by means of a motion conversion mechanism, associated both with the actuator unit and also with said at least one connection bushing, which is configured to transform the action of the actuator unit in the first direction into an alternate movement of said at least one connection bushing in a second drive direction from and toward the trolley, different from said first direction.

12 Claims, 7 Drawing Sheets

(56) References Cited

FOREIGN PATENT DOCUMENTS

| WO | WO 2009/011541 | 1/2009 |
| WO | WO 2009/016111 | 2/2009 |
| WO | WO 2012/038792 | 3/2012 |

* cited by examiner

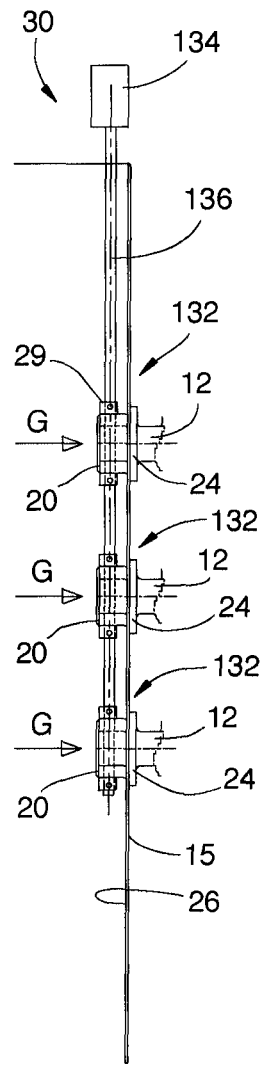
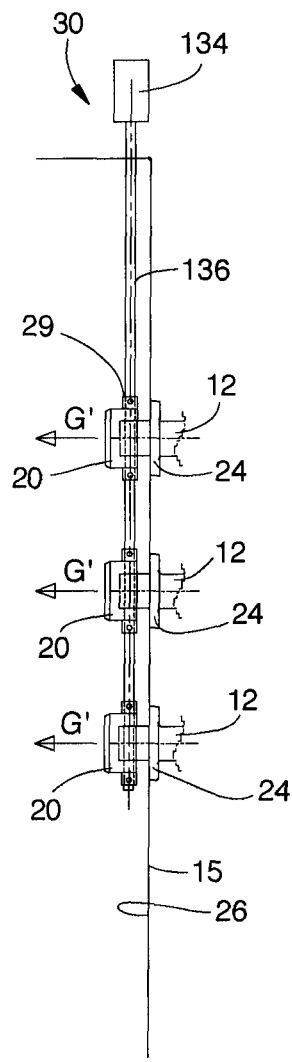
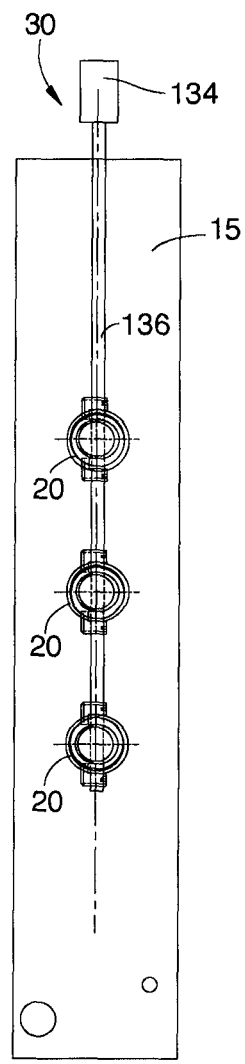
fig. 12    fig. 13    fig. 16
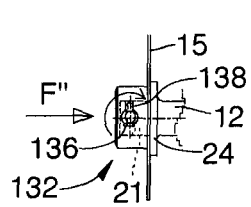
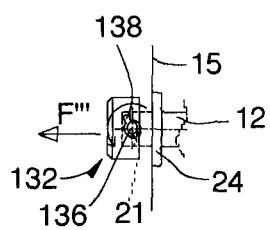
fig. 14    fig. 15

MACHINE FOR WASHING OBJECTS AND METHOD FOR THE HYDRAULIC AND MECHANICAL CONNECTION OF A TROLLEY CARRYING OBJECTS TO BE WASHED TO A FEED CIRCUIT OF A WASHING LIQUID FOR A MACHINE FOR WASHING OBJECTS

FIELD OF THE INVENTION

The present invention concerns a machine for washing objects and a method for the hydraulic and mechanical connection of a trolley carrying objects to be washed to a feed circuit of a washing liquid for a machine for washing objects.

BACKGROUND OF THE INVENTION

It is known that it is necessary to wash, disinfect, heat-disinfect, sterilize, dry and possibly package surgical or laboratory instruments or similar, which get soiled during use, so that they can be used again.

To this end, washer machines are used provided with a washing chamber which is accessible from the front, into which support trolleys are inserted for the objects to be washed, so as to carry out the necessary treatment cycle, to then be removed frontally, in the case of machines with a single door, or in a through manner in the case of machines with a double door. The trolleys have a frame which both physically supports the objects or the racks containing the objects, and also acts as a distributor circuit of the washing liquid which, by means of nozzles, impellers or similar delivery members possibly integrated in the frame of each trolley, is directed toward the objects to be treated.

Normally, the washer machines are provided with a circuit to feed the washing liquid, connected to a pump, in order to introduce the washing liquid into the distributor circuit of the trolley loaded inside the washing chamber. In particular, the feed surface faces inside the washing chamber with its delivery or coupling mouth normally connected to the plating which constitutes one of the lateral walls which delimit the washing chamber. The delivery or coupling mouth is associated to a connection bushing provided with a spring which renders it elastically yielding, and is able to be selectively moved axially with respect to the exit direction of the washing liquid, acting against the force of the spring, for a determinate segment, to then assume once again its own original position once the stress has stopped. In mating manner, the trolley has a hydraulic connection member, in a position mating with the connection bushing, for the passage of the washing liquid into the distributor circuit of the trolley. In this way, inserting the trolley into the washing chamber, the hydraulic connection member slides tangentially on the connection bushing which, due to the spring associated with it, yields elastically to allow the positioning of the trolley and, once the hydraulic connection member is aligned in position with the delivery or coupling mouth, the connection bushing itself, elastically thrust on the connection member, determines the desired mechanical and hydraulic connection. This known solution which in substance provides to keep the connection bushings constantly elastically thrust and protruding toward the inside of the washing chamber and to make the connection by means of sliding and contrast of the elastic thrust is described for example in the publication "Steelco: Washer disinfector", 14 Oct. 2011, pages 30-31.

One disadvantage of this known mechanical solution is that, when the pump is activated, the pressure of the washing liquid has a negative influence on the positioning of the connection bushing, in that, in particular, the elastic thrust of the spring is reduced. Consequently the connection bushing is not stably positioned, it distances itself from the connection member of the trolley and there is a loss or leakage of washing liquid through it, which can also generate unwanted sprays and jets of liquid since the hydraulic seal is no longer guaranteed. This loss determines a drop in pressure in the distributor circuit of the trolley and therefore a reduction in efficiency of the impellers and delivery nozzles of the washing liquid. To compensate this drop in pressure, the pump has to be acted on, with obvious waste of energy. In conclusion, the loss of washing liquid due to the unreliability of the mechanical and hydraulic connection given by the connection bushing and corresponding spring has negative effects on the final quality of the washing, as well as on the running costs of the washer machines in question. Another disadvantage is that, because of the sliding of the connection member on the connection bushing, it is not practically possible to provide packing members, such as O-rings, assembled on the latter, because the direct mechanical action of the trolley would be impeded, or in any case there would be a rapid deterioration of the packing member because of repeated friction.

Document WO-A-2009/016111 describes a hydraulic connection device for a machine for washing objects on a trolley which provides a hydraulic connection pipe protruding from an upper wall of a washing chamber and vertically mobile. This solution is not suitable to make a device for the hydraulic and mechanical connection of the type in question, and is also complex for such purpose, because the latter is installed in correspondence to one side of the washing chamber and the solution known from WO-A-2009/016111 would be excessively bulky if used laterally.

Document DE-A-10627762 also describes a washer machine which comprises an upper hydraulic connector and therefore not suitable to make a device for the hydraulic and mechanical connection of the type in question.

Purpose of the present invention is to obtain a washer machine and a method for the hydraulic and mechanical connection of a trolley carrying objects to be washed to a feed circuit of a washing liquid for a machine for washing objects which guarantees a reliable mechanical and hydraulic connection, preventing the losses of washing liquid and undesired drops in pressure known in the state of the art, and which is compact and not bulky.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

In accordance with the above purpose, a machine for washing objects according to the present invention comprises:
- a washing chamber in which to position a trolley carrying objects to be washed, which has at least a lateral wall with respect to the direction of insertion of the trolley into the washing chamber, said trolley being provided with a distributor circuit of washing liquid toward the objects to be washed;
- a feed circuit of a washing liquid toward the washing chamber;
- a device for the hydraulic and mechanical connection of the distributor circuit to the feed circuit which comprises a connection member installed on the distributor circuit, a corresponding delivery or coupling mouth installed on the feed circuit and mounted facing inside the washing chamber, on said lateral wall, and at least one connection bushing configured for connection on one side to the connection member of the distributor circuit and on the other side to the corresponding delivery or coupling mouth of the feed circuit, so as to determine the mechanical and hydraulic connection between feed circuit and distributor circuit.

The device for the hydraulic and mechanical connection of the present invention comprises:

- at least an actuator unit which is configured to selectively command the stable positioning of said at least one connection bushing acting in a first drive direction, said actuator unit comprising a motorization member and an effector member that develops longitudinally along the lateral wall of the washing chamber;
- a motion conversion mechanism, operatively connected both to the effector member of the actuator unit and also to said at least one connection bushing, which is configured to convert the action of the actuator unit in the first direction into an alternate movement of said at least one connection bushing in a second drive direction, from and toward the trolley, different from said first direction.

In some forms of embodiment, the actuator unit is configured to command the position of the connection bushing so that the latter, as a function of the drive of said actuator unit and the correlated alternate movement, has a finite number of stable positions, of which at least one first stable position in which said connection bushing is released from said connection member and is sufficiently displaced toward said delivery or coupling mouth so as to allow the trolley to be inserted without interference inside the washing chamber, and a second stable operating position, more distanced, or protruding, from said delivery or coupling mouth with respect to said first operating position, in which it is configured to engage said connection member of the trolley for a mechanical and hydraulic seal.

With the present invention, when the trolley is not inserted in the washing chamber the one or more connection bushings are in their first position and do not protrude toward the inside and therefore they do not slide on the trolley when this is inserted. Moreover, with the present invention the one or more connection bushings, once moved and connected to corresponding connection members of the trolley, are kept stably in the second operating position, in which they achieve a reliable mechanical and hydraulic coupling with the connection member of the trolley, thanks to the actuator unit, which is configured to stably position the connection bushings, on each occasion in the desired positions, and also to support possible alterations of pressure deriving from the use of the pump associated to the feed circuit of the washing liquid.

In this manner, an unwanted movement of the one or more connection bushings from their operating condition is prevented, which could cause loss of washing liquid, and therefore loss of pressure of the liquid fed to the delivery nozzles and impellers of the washing liquid provided on the trolley.

The constancy of the pressure of the washing liquid in the distributor circuit of the trolley is thus guaranteed substantially under any condition, and therefore optimal effectiveness of the impellers and nozzles is obtained, achieving an efficient washing without wasting liquid or energy in the functioning of the pump.

Moreover, in this way, when the trolley is inserted in the washing chamber, it does not interfere with the connection bushings, given that the latter are stably in the first retracted position, and it is thus possible to provide the use of packings between the connection bushings and delivery or coupling mouths, which greatly increase the guarantee of hydraulic seal.

Moreover, having to install the mechanical and hydraulic connection device in question on one side of the washing chamber, so that it is correctly configured to cooperate with the trolley which is inserted, it is advantageous to provide that the drive of the actuator unit and the movement of the connection bushings are in different directions, thanks to the motion conversion mechanism described above, since, by suitably disposing the actuator unit with respect to the connection bushings, the mechanical and hydraulic connection device itself is rendered more compact laterally.

In a variant, the first drive direction of the actuator unit is linear and the motion conversion mechanism is configured to convert the linear motion of the actuator unit into a linear motion of the one or more connection bushings from and toward the trolley.

According to another variant the first drive direction of the actuator unit is rotatory, or angular, and the motion conversion mechanism is configured to convert the rotatory motion of the actuator unit into a linear motion of the one or more connection bushings from and toward the trolley. In particular, a motorization member can be provided, for example an electric one, protected to safely resist conditions of humidity and temperature associated to the washer machine, configured to determine the linear or rotatory motion of the actuator unit associated to the connection bushings.

The present invention also concerns a method for the hydraulic and mechanical connection of a distributor circuit of a trolley carrying objects to be washed in a machine for washing objects to a feed circuit of a washing liquid toward a washing chamber of the washer machine. The method provides to selectively activate an actuator unit in order to cause the commanded positioning of at least one connection bushing disposed on one side of the washing chamber and configured for connection on one side to a connection member of the distributor circuit and on the other side to a corresponding delivery and coupling mouth of the feed circuit, said actuator unit selectively cooperating with said at least one connection bushing and acting in a first drive direction, a motion conversion mechanism being used, operatively connected both to the actuator unit and also to said at least one connection bushing, which converts the action of the actuator unit in the first direction into an alternate movement of said at least one connection bushing in a second drive direction, from and toward the trolley, different from said first direction.

BRIEF DESCRIPTION OF THE DRAWINGS

These and other characteristics of the present invention will become apparent from the following description of forms of embodiment, given as a non-restrictive example with reference to the attached drawings wherein:

FIG. 12 is an enlarged detail of FIG. 10;

FIG. 13 is an enlarged detail of FIG. 11;

FIG. 14 is a view from above of FIG. 12;

FIG. 15 is a view from above of FIG. 13;

FIG. 16 is a front view of part of the device in FIG. 8;

Figure 2:
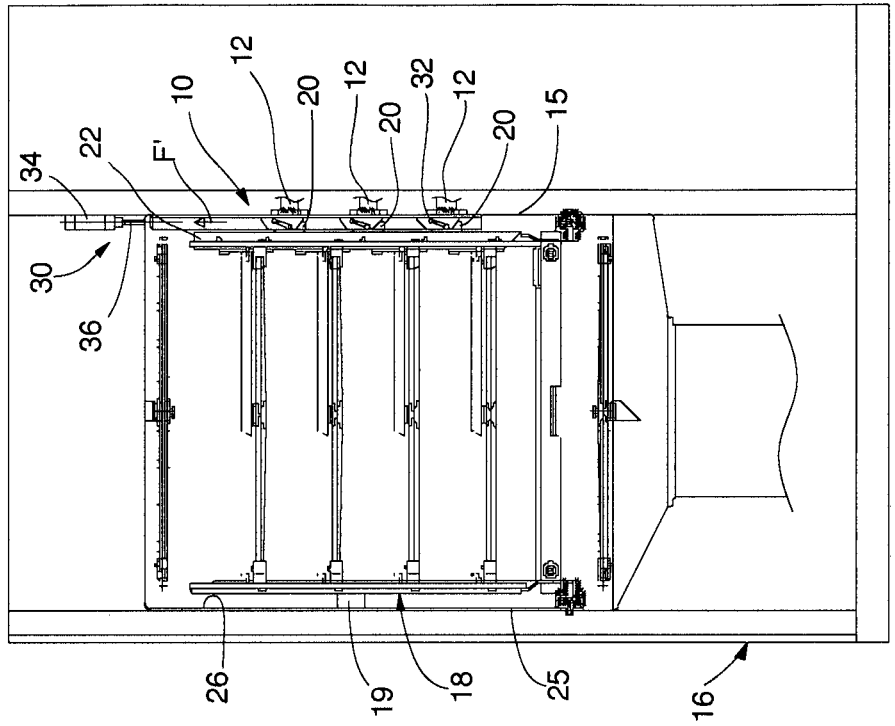
FIG. 2 is a schematic view of the device in FIG. 1 in a second condition.
Figure 1:
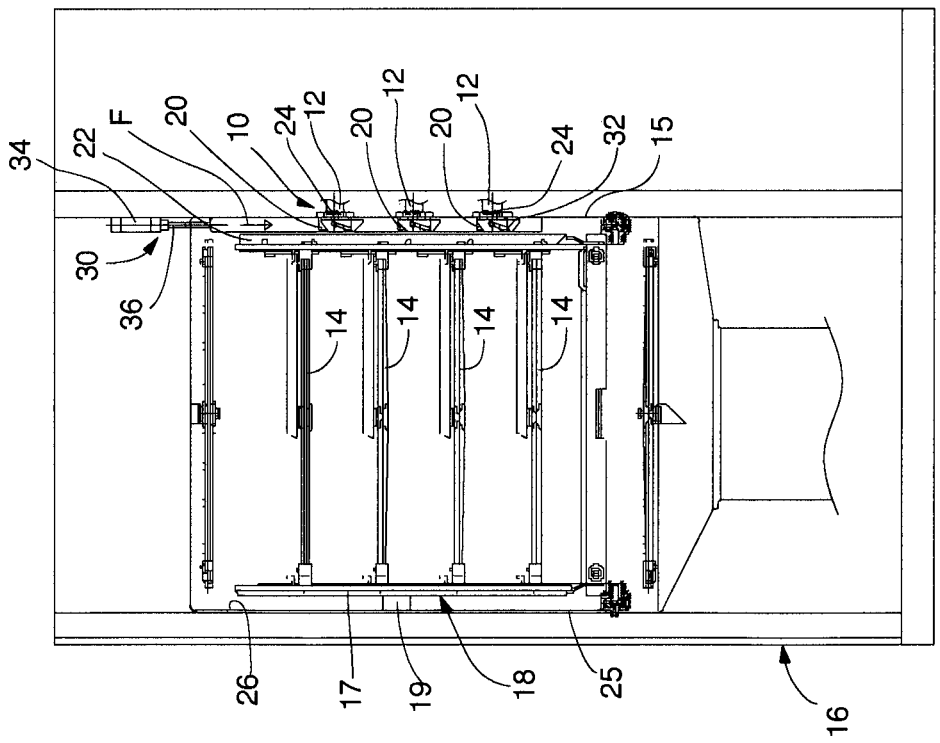
FIG. 1 is a schematic view of a first form of embodiment of a washer machine which includes a device according to the present invention in a first condition.
Figure 4:
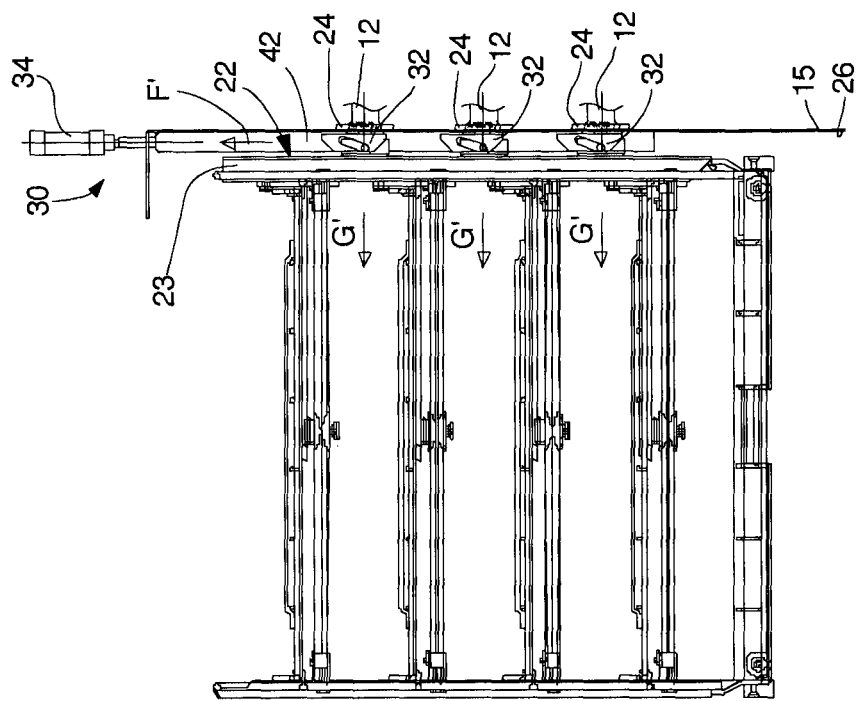
FIG. 4 is an enlarged schematic view of FIG. 2.
Figure 3:
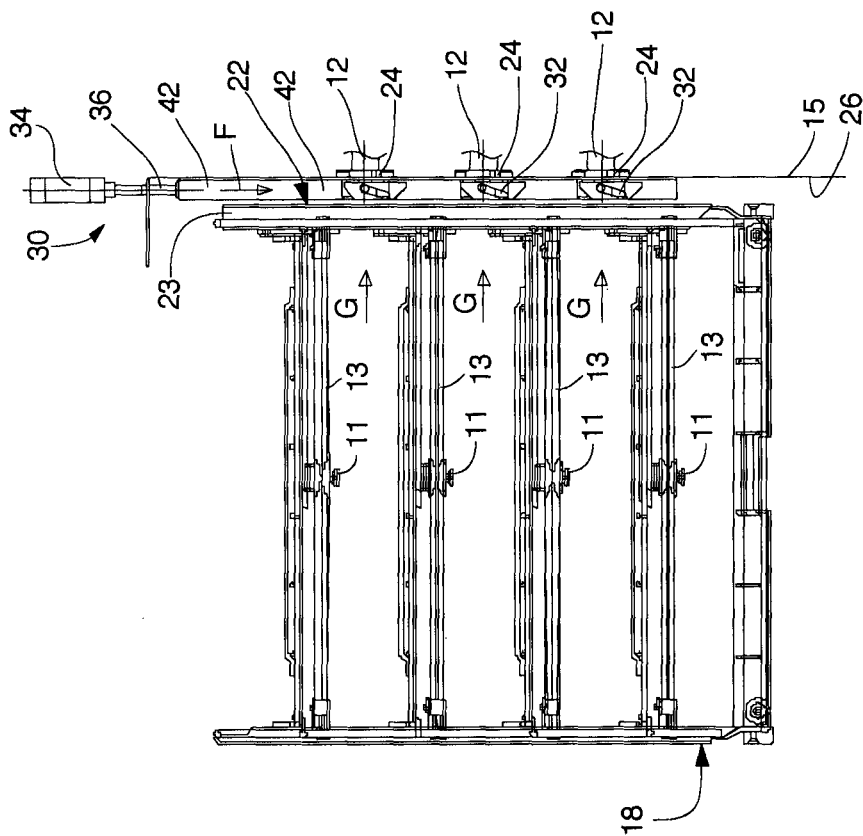
FIG. 3 is an enlarged schematic view of FIG. 1.
Figure 5:
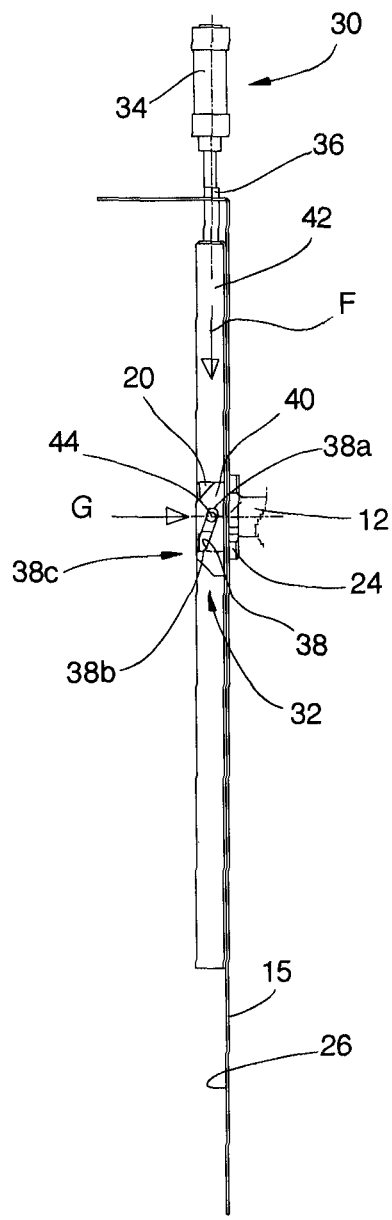
FIG. 5 is an enlarged detail of FIG. 3.

To facilitate comprehension, the same reference numbers have been used, where possible, to identify identical common elements in the drawings. It is understood that elements and characteristics of one form of embodiment can conveniently be incorporated into other forms of embodiment without further clarifications.

DESCRIPTION OF SOME FORMS OF EMBODIMENT

With reference to the attached drawings, a machine 16 for washing objects according to the present invention comprises a washing chamber 26 inside which the objects are washed by a washing liquid and a device 10, 110 used for the hydraulic and mechanical connection of a distributor circuit 14 of washing liquid of a trolley or rack 18 carrying objects to be washed to a feed circuit 12 of a washing liquid of the machine 16 for washing objects.

The feed circuit 12 is hydraulically associated with a pump to feed the washing liquid, not shown in the drawings.

The distributor circuit 14 is integrated in a frame 17 to support and move the trolley 18 which positions support planes or elements for the object-bearing trolleys, or to position the objects to be washed directly. The distributor circuit 14 may comprise nozzles 11 and/or impellers 13 to deliver the washing liquid.

In some forms of embodiment, the device 10, 110 is disposed lateral, for example installed on an internal lateral wall 15 of the washing chamber 26 provided in the washer machine 16. The washing chamber 26 is for example accessible from the front through a desired aperture. In some forms of embodiment a washer machine 16 with a single door may be provided, in which the front aperture is used to insert and remove the trolley 18, or, in other forms of embodiment, with a double pass-through door, in which there is a front aperture with a corresponding door, for the entry of the trolley 18, and a rear aperture with corresponding door, to remove the trolley 18 when the treatment of the objects is finished.

The device 10, 110 according to the present invention comprises at least one mobile connection bushing 20, associable, that is, connectable, mechanically and hydraulically, on one side to a connection member 22 of the distributor circuit 14 and on the other side to at least a delivery or coupling mouth 24 of the feed circuit 12 which faces, through the lateral wall 15, inside the washing chamber 26 of the washer machine 16.

In some forms of embodiment, the device 10, 110 comprises a plurality of connection bushings 20, associated with a mating plurality of delivery or coupling mouths 24 distributed along the lateral wall 15 and served by a pump for feeding the washing liquid, not shown in the drawings. In the solution shown by way of example in the drawings, three connection bushings 20 and three corresponding delivery or coupling mouths 24 are provided.

In this case, the connection member 22 comprises for example a hydraulic collector 23. The hydraulic collector 23 can develop in this case longitudinally along the lateral wall 15 when the trolley 18 is in the washer machine 16. The hydraulic collector 23 is provided with inlets, not visible in the drawings, by means of which the washing liquid can flow from the feed circuit 12 inside the distributor circuit 14, where it is delivered onto the objects to be washed by the nozzles 11 and/or impellers 13.

According to the present invention, the device 10, 110 comprises at least an actuator unit 30 that selectively cooperates with said at least one connection bushing 20.

An actuator unit 30 is configured to transform an input signal, typically electric, into a defined movement or drive. In possible forms of embodiment, an actuator unit can include a mechanical actuator, for example of the screw or female screw type, or with a toothed wheel and linear axis, or a cam, or a hydraulic actuator, such as for example a cylinder-piston unit, a pneumatic actuator, an electro-mechanical actuator, in which a mechanical actuator is connected to an electric motor to control the movement, or a piezoelectric actuator or suchlike. An electric motor can be chosen from a group that includes a continuous current motor, with or without brushes, or a step motor, or an alternate current motor, for example a synchronous motor, a brushless synchronous motor, an asynchronous motor, a mono-phase motor or a tri-phase motor, or an induction motor. Additionally, it may be provided to use an encoder or similar sensor, to have a precise displacement.

The actuator unit 30 is configured to act in a first drive direction F, F', F'', F'''. The cooperation between the actuator unit 30 and the connection bushing 20 is determined by a kinematic motion conversion mechanism 32, 132, associated both with the actuator unit 30 and the connection bushing 20, which is configured to convert the drive movement of the actuator unit 30 in the first direction (F, F', F'', F''') into a an alternate movement of the connection bushing 20 in a second drive direction G, G', from and toward the trolley 18.

In particular, the actuator unit 30 comprises a motorization member 34, 134 and an effector member 36, 136, to which the kinematic motion conversion mechanism 32, 132 is associated.

The actuator unit 30 can be the electro-mechanical type and the motorization member 34, 134 can be an electric motor.

The effector member 36, 136 develops longitudinally along the lateral wall 15 of the washing chamber 26 on which the device 10, 110 is installed. The effector member 36, 136, suitably driven by the motorization member 34, 134, acts on the kinematic conversion mechanism 32, 132.

Since the connection bushing 20 is mobile, it has, depending on the drive of the actuator unit 30 and the correlated alternate movement, a finite number of stable positions, of which at least a first stable position (FIGS. 1, 3, 5 and 8, 10, 12), in which the connection bushing 20 is released from the connection member 22 and is sufficiently displaced, or retracted, toward the delivery or coupling mouth 24 to allow the trolley 18 to be inserted without interference inside the washing chamber 26, and a second stable operating position (FIGS. 2, 4 6 and 9, 11, 13), more distanced or protruding from the delivery or coupling mouth 24 with respect to said first operating position, in which it is able to engage the connection member 22 of the trolley 18 to obtain the mechanical and hydraulic seal, so that there are no leakages of liquid in the passage from the feed circuit 12 to the distributor circuit 14.

In some forms of embodiment, on a lateral wall 25, opposite the lateral wall 15, there is a positioner element 19, such as a block suitably attached to the lateral wall 25, which cooperates with the trolley 18, determining a counter-thrust or abutment, to compensate the thrust action exerted when the connection bushing 20 engages the trolley 18 in the second position, in this way preventing any unwanted positioning, oscillations or lateral sideslipping of the trolley 18.

With reference to FIGS. 1-7 we shall now describe a first form of embodiment of the device according to the present invention, indicated for convenience by the reference number 10.

In the first form of embodiment, the actuator unit 30 is driven linearly and the effector member is a cylinder-piston unit 36, of the linear mechanical type, fluid-dynamic, pneumatic or analogous linear mechanical actuator.

The motorization member or motor indicated by the reference 34, determines an alternate linear motion of the cylinder-piston unit 36.

The cylinder-piston unit 36 is connected to the kinematic motion conversion mechanism, which in this first form of embodiment is indicated by the reference number 32. The alternate linear motion in the first direction F (downward), F' (upward) of the cylinder-piston unit 36 is thus converted by the kinematic motion conversion mechanism 32 into a movement in a second direction G (outward), G' (inward). In some forms of embodiment, the kinematic motion conversion mechanism 32 comprises inclined eyelets 38 with a linear development with a desired length to define a determinate travel. For example the inclined eyelets 38 in this case are inclined downward from the lateral wall 15 toward the inside of the washing chamber 26.

The inclined eyelets 38 are made in this case on support plates 40. In particular, in the first form of embodiment a plurality of pairs of support plates 40 are provided, associated with a support and movement frame 42 (FIG. 7) connected to the cylinder-piston unit 36. The support plates 40 are distributed uniformly in length, in desired positions with respect to the location of the delivery or coupling mouths 24.

Each pair of support plates 40 provides two plates, disposed facing on one side and the other with respect to the bar 36, so that the inclined eyelets 38 are aligned on one side and the other, defining a guided sliding or linear translation plane in a travel between two ends, upper 38a and lower 38b of each inclined eyelet 38. Each inclined eyelet 38 has a front aperture 38c, in this case in correspondence with the lower end 38b.

Figure 6:
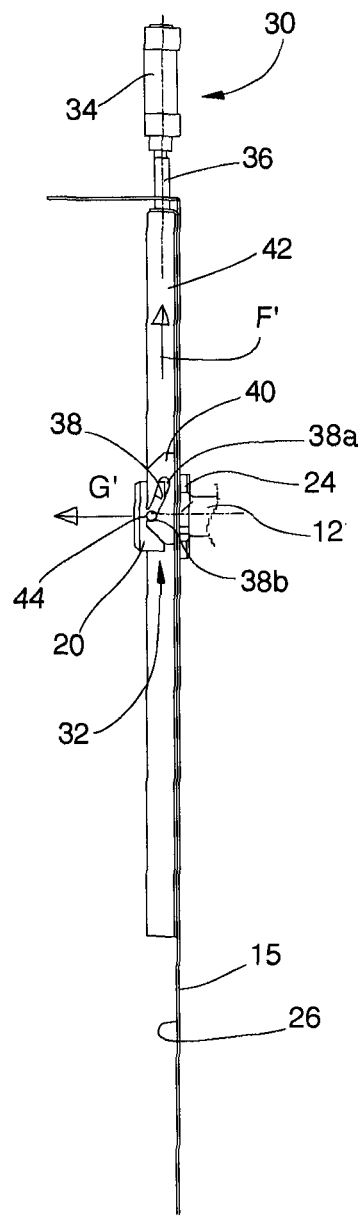
FIG. 6 is an enlarged detail of FIG. 4.
Figure 7:
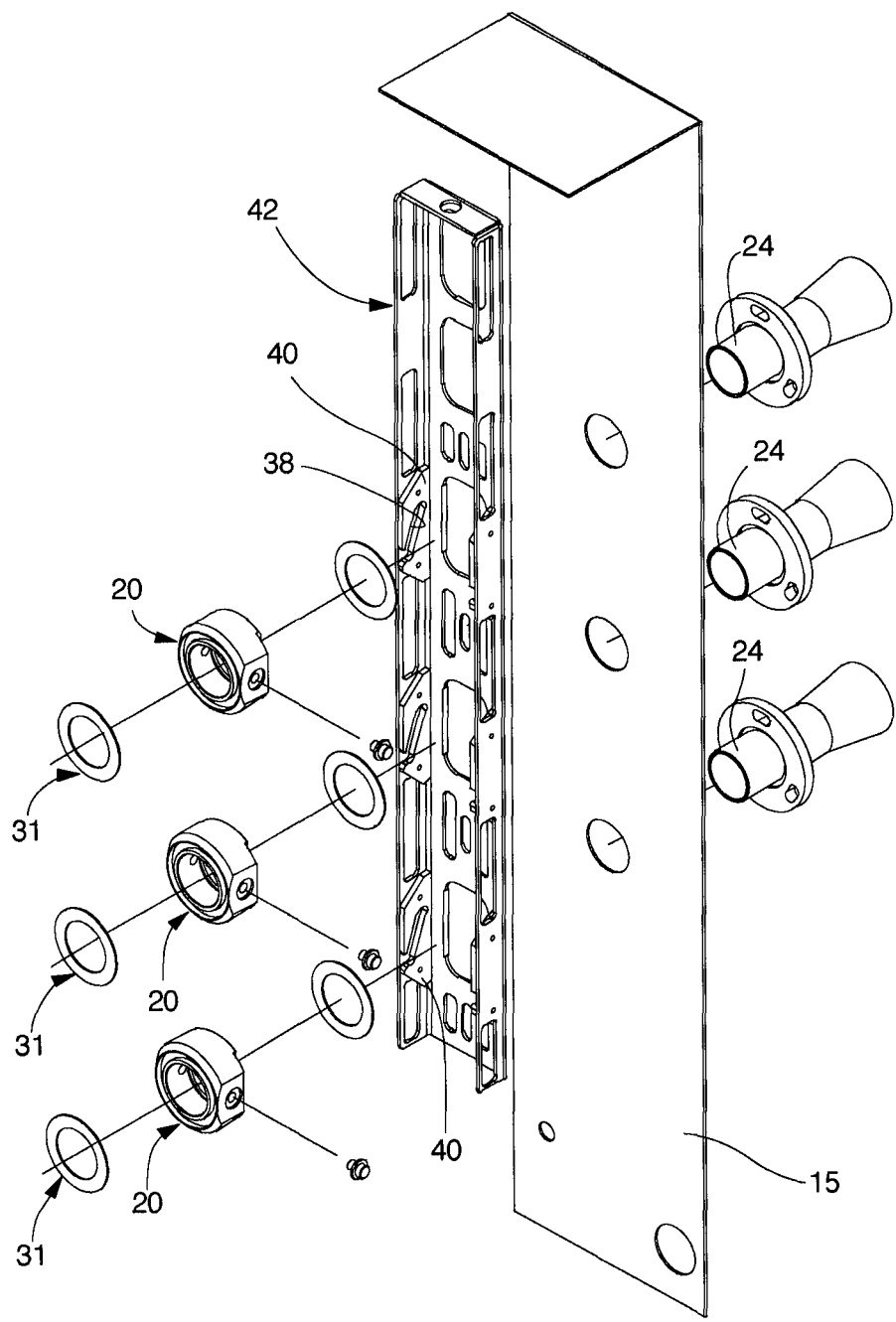
FIG. 7 is a view in separate parts of part of the device in FIG. 1.
Figure 9:
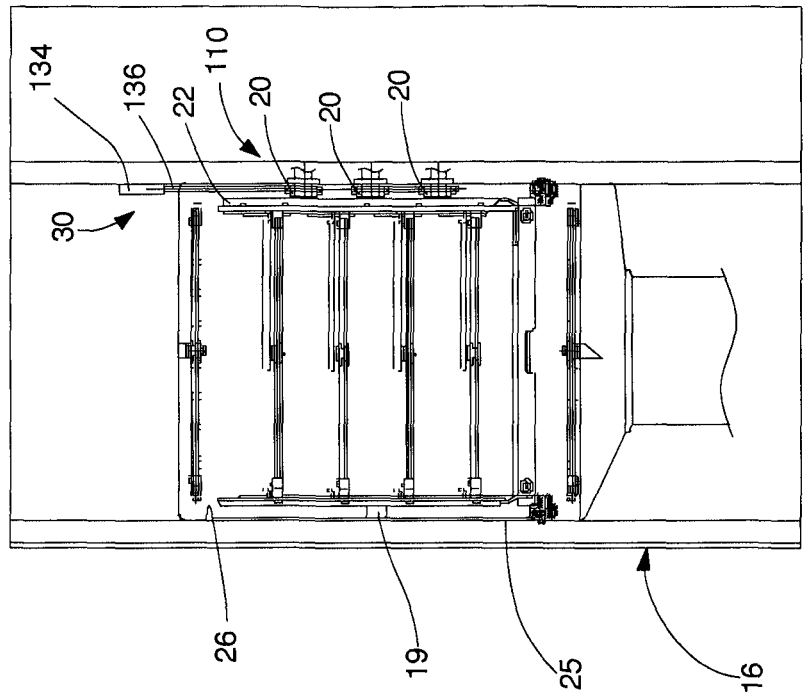
FIG. 9 is a schematic view of the device in FIG. 8 in a second condition.
Figure 8:
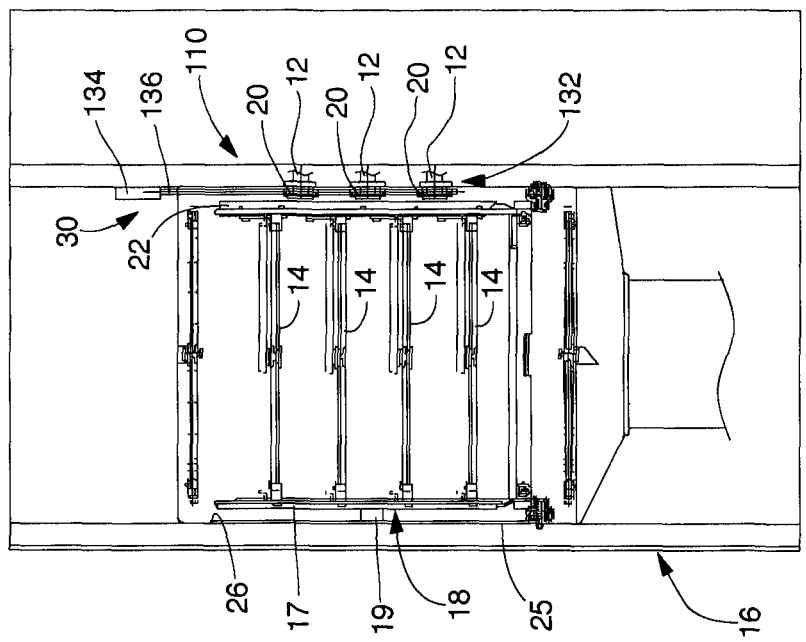
FIG. 8 is a schematic view of a second form of embodiment of a washer machine which includes a device according to the present invention in a first condition.
Figure 11:
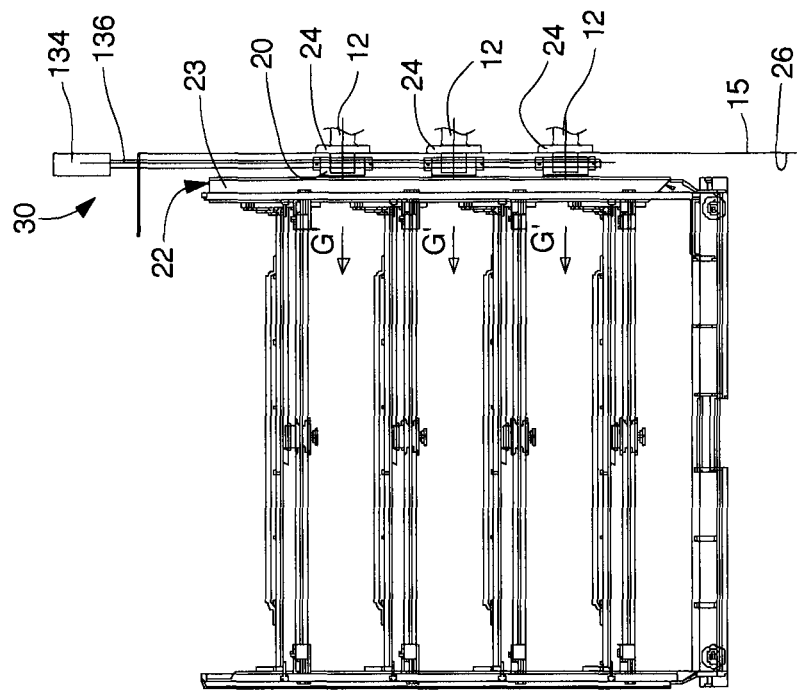
FIG. 11 is an enlarged schematic view of FIG. 9.
Figure 10:
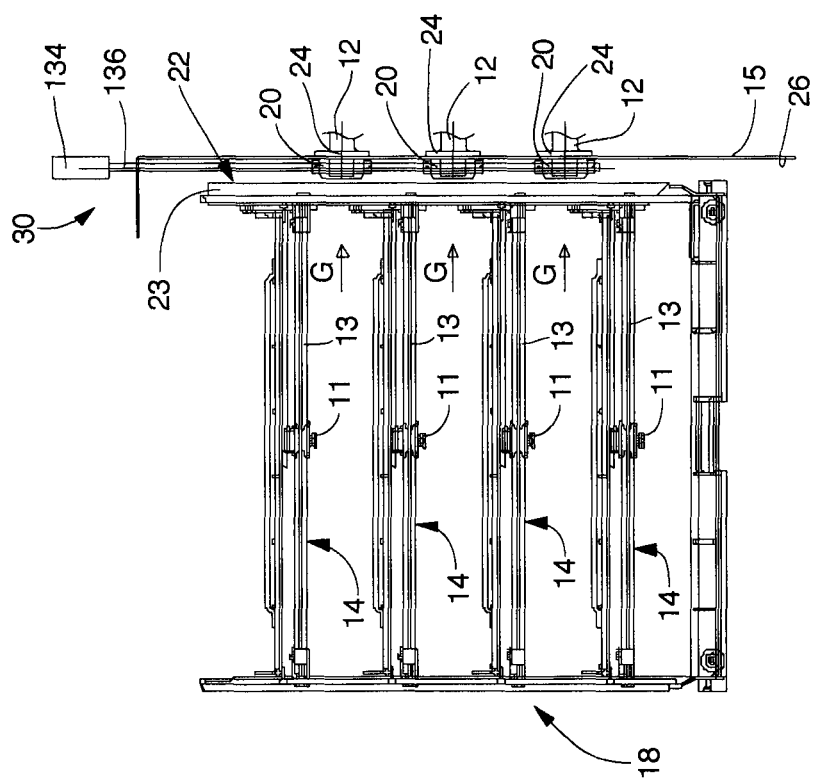
FIG. 10 is an enlarged schematic view of FIG. 8.

Since in this case the inclined eyelets 38 face downward, the upper end 38a is nearer the lateral wall 15 and is associated with the first position of the connection bushing 20 (FIG. 5), while the lower end 38b is more distant from the lateral wall 15 and is associated with the second position of the connection bushing 20 (FIG. 6).

In particular, the motorization member 34 moves the effector member 36 linearly, which in turn determines the movement of the support and movement frame 42 and hence of the support plates 40.

In the first form of embodiment, each connection bushing 20 has laterally a pair of pegs or pins 44, suitable to cooperate sliding inside and along the inclined eyelets 38. In particular, in order to mount each connection bushing 20, the apertures 38c of the inclined eyelets 38 are used, inserting the pegs or pins 44 through them.

The linear displacement, upward or downward, of the support and movement frame 42 takes the inclined eyelets 38 into interference against the pegs or pins 44 of each connection bushing 20 and, due to the particular inclined conformation, the linear motion of the support and movement frame 42 in the first direction F (downward), F (upward) is converted into the axial motion of the connection bushing 20 in the second direction G (outward), G' (inward), leading to selectively engage the connection member 22 of the trolley. In particular, the connection bushings 20 are positioned in the second stable operating condition, in which they cooperate both hydraulically and mechanically with the inlets of the hydraulic collector 23 of the connection member 22 of the trolley 18.

The second movement direction G, G' of the connection bushings 20 is understood overall as the result given by the conformation of the inclined eyelets 38, of one vertical movement and one horizontal one.

In the case of several connection bushings 20, the sole support and movement frame 42 connected to the cylinder-piston unit 36 is configured to determine the simultaneous and synchronous positioning of the connection bushings 20 in the desired positions with a single linear movement downward or upward.

With reference to FIGS. 8-16 we shall now describe a second form of embodiment of the device according to the present invention, indicated for convenience by the reference number 110.

In the second form of embodiment, the actuator unit 30 is driven angularly and the effector member is a longitudinal bar 136, rotating on itself around a central axis that develops during use along the lateral wall 15 of the washer machine 16. The longitudinal bar 136 is located through, through passage windows 29 of the respective connection bushings 20 mounted aligned with the corresponding delivery or coupling mouths 24 of the lateral wall 15.

The motorization member, or motor, indicated in this case by the reference number 134, determines an alternate rotational motion of the longitudinal bar 136. The kinematic motion conversion mechanism, in this second form of embodiment indicated by the reference number 132, comprises a rotary peg or tooth 138 associated with the longitudinal bar 136 for each connection bushing 20.

Each rotary peg or tooth 138 is located in an internal cavity 21 of the corresponding connection bushing 20. The rotary peg or tooth 138 of each connection bushing 20, due to the rotation imparted by the longitudinal bar 136 in one direction or the other, has at least two angular positions, different and rotated one with respect to the other, associated with the first and second operating position of the connection bushing 20. As can easily be seen in FIGS. 14 and 15, in a first angular position the rotary peg or tooth 138 (FIG. 14) extends parallel to the lateral wall 15, not interfering with the connection bushing 20, which therefore rests in its first position in which it is substantially retracted toward the lateral wall (FIG. 12).

On the contrary, in a second angular position the rotary peg or tooth 138 (FIG. 15) extends transverse to the lateral wall 15, protruding as much as necessary, in relation to its length, to interfere with the connection bushing 20, thrusting it into its second position in which it engages the corresponding inlet of the hydraulic collector 23 of the connection member 22 of the trolley 18 (FIG. 13).

By selectively rotating the longitudinal bar 136 in a clockwise or anti-clockwise direction respectively in the first direction F''' (clockwise), F''' (anti-clockwise) (FIGS. 14, 15), it is possible to pass from the first to the second position of the connection bushings 20, moved respectively in the second direction G (outward), G' (inward), in a desired manner, depending on whether it is necessary to insert the trolley 18 into the washing chamber 26 or to connect or disconnect the trolley 18 hydraulically and mechanically to/from the feed circuit 12.

In this case too, with several connection bushings 20, the single longitudinal bar 136 is configured to determine the simultaneous and synchronous positioning of the connection bushings 20 in the desired positions with a single rotation in one direction or the other.

Advantageously, thanks to the present invention, it is possible with both the first and second form of embodiment, to position a hydraulic sealing packing 31, for example an O-ring, between each connection bushing 20 and the connection member 22, to increase the guarantee of a hydraulic seal and prevent the leakage of washing liquid. In fact, when the trolley 18 is inserted into the washing chamber 26, the connection bushings 20 are in the first position, more retracted toward the lateral wall 15, and therefore they do not interfere with the trolley 18. Consequently, the hydraulic seal packing 31 is also protected from sliding, wear or other that could ruin it or cause it to detach, as happens in the state of the art.

According to a variant form of embodiment, the drive of the actuator unit 30 may be kinematically associated by means of a suitable return mechanism, either mechanical, electro-mechanical or suchlike, to the opening and closing movement of the door installed on the loading aperture through which the trolley 18 is inserted into the washing chamber 26 and/or to the rear closing door, in the case of a double-door washer machine, so that, when the door is opened, the connection bushing 20 is in the first position, and the trolley 18 can therefore be inserted freely, and, when the door is closed, the connection bushing 20 is in the second position, achieving the mechanical and hydraulic coupling of the feed circuit 12 and the distributor circuit 14.

The invention claimed is:

1. A machine for washing objects, comprising:
   a washing chamber in which to position a trolley carrying objects to be washed, which has at least a lateral wall with respect to a direction of insertion of the trolley into the washing chamber, said trolley being provided with a distributor circuit for distributing washing liquid toward the objects to be washed;
   a feed circuit for feeding a washing liquid toward the washing chamber;
   a device for the hydraulic and mechanical connection of the distributor circuit to the feed circuit which comprises a connection member installed on the distributor circuit, a corresponding delivery or coupling mouth installed on the feed circuit and mounted facing inside the washing chamber on said lateral wall, and at least a connection bushing configured for connection on one side to the connection member of the distributor circuit and on the other side to the corresponding delivery or coupling mouth of the feed circuit, so as to determine the mechanical and hydraulic connection between feed circuit and distributor circuit, wherein the device for the hydraulic and mechanical connection comprises:
   at least an actuator unit which is configured to selectively command the stable positioning of said at least one connection bushing acting in a first drive direction, said actuator unit comprising a motorization member and an effector member that develops longitudinally along the lateral wall of the washing chamber; and
   a motion conversion mechanism, operatively connected both to the effector member of the actuator unit and also to said at least one connection bushing, which is configured to convert the action of the actuator unit in the first direction into an alternate movement of said at least one connection bushing in a second drive direction, from and toward the trolley, different from said first direction.

2. The machine as in claim 1, wherein said actuator unit is configured to command the position of said at least one connection bushing so that said connection bushing, as a function of the drive of said actuator unit and of the correlated alternate movement, has a finite number of stable positions, of which at least a first stable position in which said at least one connection bushing is released from said connection member and is sufficiently displaced toward said delivery or coupling mouth to allow the trolley to be inserted without interference inside the washing chamber, and a second stable operating position, more distanced from said delivery or coupling mouth compared with said first operating position, in which it is configured to engage said connection member of the trolley for a mechanical and hydraulic seal.

3. The machine as in claim 1, wherein the first drive direction of the actuator unit is linear and said motion conversion mechanism is configured to convert the linear motion of the actuator unit into a linear motion in the second direction from and toward the trolley of the one or more connection bushings.

4. The machine as in claim 3, wherein the effector member comprises a cylinder-piston unit and the motorization member is suitable to determine an alternate linear motion of the cylinder-piston unit.

5. The machine as in claim 4, wherein the motion conversion mechanism comprises inclined eyelets with a linear development along a determinate travel between two upper and lower ends, which are made on support plates associated with a support and movement frame connected to the cylinder-piston unit and provided in desired positions with respect to the location of the delivery or coupling mouths.

6. The machine as in claim 5, wherein each connection bushing has laterally a pair of pegs or pins suitable to cooperate sliding inside the inclined eyelets along the travel defined by the upper end, in which the connection bushing assumes the first position, and the lower end, in which the connection bushing assumes the second position.

7. The machine as in claim 2, wherein the first drive direction of the actuator is rotatory and said motion conversion mechanism is configured to convert the rotatory motion of the actuator unit into a linear motion along the second direction from and toward the trolley of the one or more connection bushings.

8. The machine as in claim 7, wherein the effector member comprises a longitudinal bar, rotating on itself around a central axis, and the motorization member is configured to determine an alternate angular motion of the longitudinal bar.

9. The machine as in claim 8, wherein, for each connection bushing, the motion conversion mechanism comprises a rotary pin or tooth associated with the longitudinal bar, positioned in an internal cavity of the corresponding connection bushing and having, by means of the rotation imparted by the rotary bar in one direction or the other, at least two different angular positions, rotated one with respect to the other and associated with the first and second operating position of the connection bushing.

10. The machine as in claim 9, wherein in a first angular position the rotary pin or tooth extends parallel to the lateral wall and in a second angular position the rotary pin or tooth extends transverse to the lateral wall, interfering with the connection bushing so as to thrust it into the corresponding second position.

11. The machine as in claim 1, wherein the device for the hydraulic and mechanical connection comprises a hydraulic seal packing located between each connection bushing and the corresponding delivery or coupling mouth.

12. A method for washing objects, comprising:
   a hydraulic and mechanical connection of a distributor circuit of a trolley carrying objects to be washed in a washer machine of objects to a feed circuit of a washing liquid toward a washing chamber of the washer machine, selectively activating an actuator unit to cause a commanded positioning of at least one connection bushing disposed on one side of the washing chamber and configured for connection on one side to a connection member of the distributor circuit and on the other side to a corresponding delivery or coupling mouth of the feed circuit mounted inside the washing chamber, said actuator unit comprising a motorization member and an effector member that develops longitudinally along the lateral wall of the washing chamber, selectively cooperating with said at least one connection bushing and acting in a first drive direction, a motion conversion mechanism, operatively connected both to the actuator unit and to said at least one connection bushing, for converting the acting of the actuator unit in the first direction into an alternate movement of said at least one connection bushing in a second drive direction, from and toward the trolley, different from said first direction.

\* \* \* \* \*